United States Patent
Heene et al.

(10) Patent No.: US 6,462,812 B1
(45) Date of Patent: Oct. 8, 2002

(54) GOLF BALL INDICIA VERIFICATION SYSTEM

(75) Inventors: Kevin A. Heene, Carlsbad, CA (US); David C. Stewart, Carlsbad, CA (US)

(73) Assignee: Callaway Golf Company, Carlsbad, CA (US)

(*) Notice: Subject to any disclaimer, the term of this patent is extended or adjusted under 35 U.S.C. 154(b) by 2 days.

(21) Appl. No.: 09/718,274

(22) Filed: Nov. 21, 2000

(51) Int. Cl.⁷ .......................... G01N 21/00; G06K 9/00
(52) U.S. Cl. ............... 356/237.1; 382/141; 382/216
(58) Field of Search .................. 356/237.1; 382/141, 382/216, 218; 473/132, 378; 73/865.8

(56) References Cited

U.S. PATENT DOCUMENTS

| | | | | |
|---|---|---|---|---|
| 5,395,174 A | * | 3/1995 | Koch et al. | 156/384 |
| 5,580,318 A | * | 12/1996 | Weber | 473/137 |
| 5,632,205 A | * | 5/1997 | Gordon et al. | 101/483 |
| 5,703,687 A | * | 12/1997 | Kumagai et al. | 356/426 |
| 5,755,335 A | * | 5/1998 | Michelotti et al. | 198/394 |
| 5,777,244 A | * | 7/1998 | Kumagai et al. | 73/865.8 |
| 5,848,189 A | | 12/1998 | Pearson et al. | |
| 5,859,923 A | | 1/1999 | Petry, III et al. | |
| 6,031,933 A | * | 2/2000 | Kumagai | 356/426 |
| 6,061,086 A | | 5/2000 | Reimer et al. | |
| 6,319,563 B1 | * | 11/2001 | Skrabski et al. | 427/261 |

* cited by examiner

Primary Examiner—Zandra Smith
(74) Attorney, Agent, or Firm—Michael A. Catania

(57) ABSTRACT

A system for inspecting indicia on a golf ball is disclosed herein. The system uses a multitude of cameras to analyze indicia that has been printed on the surface of the golf ball in order to accept or reject each golf ball. In a preferred embodiment, the system is placed in-line with the printing of the indicia on the golf ball surface, and prior to the curing of the indicia in order to easily remove unacceptable indicia.

15 Claims, 8 Drawing Sheets

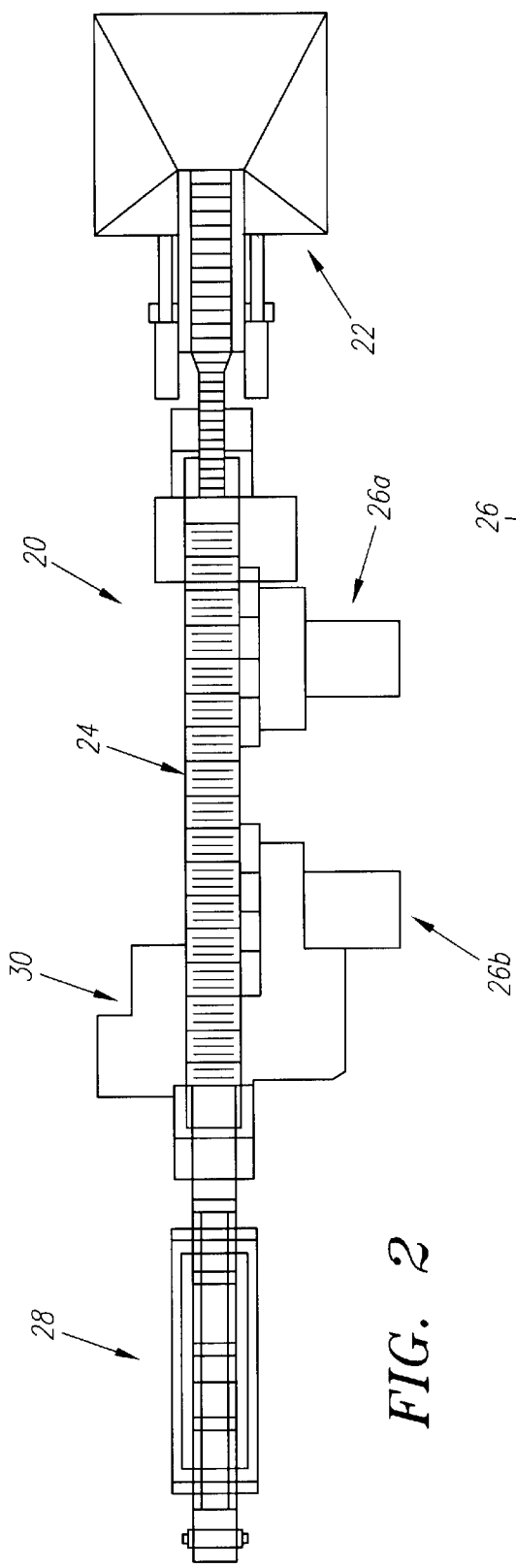
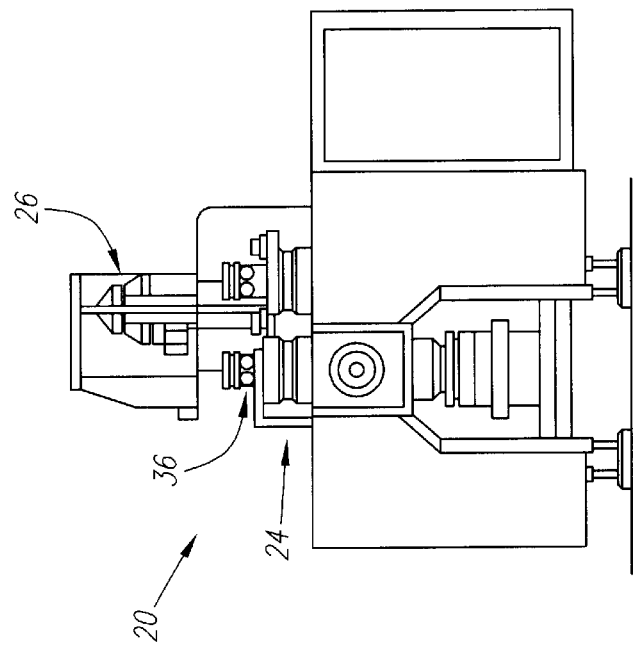
FIG. 2
FIG. 3

GOLF BALL INDICIA VERIFICATION SYSTEM

CROSS REFERENCES TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

The present invention relates to a visual verification system. More specifically, the present invention relates to a visual verification system for golf ball indicia.

2. Description of the Related Art

Golf balls have indicia such as logos, brand names and the like to identify the golf ball and its source of origin. The indicia are typically printed on a base-coated surface of the cover of the golf ball, and covered with a top-coating to prevent damage during impact with a golf club. Thus, the indicia must have a perfect appearance since it is often the most distinctive quality of a golf ball.

The current inspection process is visual inspection of the indicia subsequent to top-coating. Thus, it is not until the golf ball is ready for packaging that the indicia is inspected for appearance and quality.

Automated vision inspection systems have been utilized in many industries to increase production times. Typically, a predetermined digital image is compared to the product to be inspected by the vision system. The vision system will look for differences in contrast, brightness, proportions, discontinuations, and the like. When a variance is discovered, the system will reject the inspected product. Although such systems have found acceptance in various industries, the golf ball industry has failed to develop such a vision inspection system due to unique problems associated with the golf ball industry.

First, current indicia printing systems employed in the golf ball industry do not have sufficient space to enable any type of vision inspection system. Second, most indicia printing systems in the golf ball industry employ inks that necessitate curing prior to vision inspection and thus inspection is rendered partially ineffective since the only possibility is to reject the golf ball. Thirdly, a golf ball is a dimpled spherical unit that has indicia printed on several areas of the sphere. A vision inspection system must be able to rotate the golf ball to provide inspection of all of the golf ball's indicia, and the system must be able to compare the correct areas to those being inspected to prevent rejection of good golf balls. Fourthly, the vision inspection system must not ruin the indicia through its inspection of the indicia, or rotation of the golf ball to inspect the indicia. Fifthly, the system must be capable of inspecting at a speed that does not interrupt the production cycle. The inspection system should not be the production time determinate. Those skilled in the art also recognize the many other problems associated with vision inspection of golf ball indicia.

BRIEF SUMMARY OF THE INVENTION

The present invention is a system designed for vision inspection of golf ball indicia that provides a solution to all of the unique problems associated with vision inspection of golf ball indicia. The present invention allows for non-altering vision inspection of all of the golf ball's indicia without reducing production time. The present invention also provides a mechanism for in-line rejection of defective indicia golf balls to remove and re-print the indicia.

One aspect of the present invention is a method for inspecting golf ball indicia. The general method commences with transferring a golf ball to a vision inspection station. The golf ball has indicia printed thereon. Next, the golf ball is maneuvered to position the indicia within viewing of a first camera within the vision inspection system. Next, the indicia is scanned and an image of the indicia is transferred to a computer for inspection of the indicia. Then, the image is analyzed to determine if the indicia is within acceptable parameters.

Another aspect of the present invention is a method for in-line inspection of golf ball indicia. The method begins with transferring a golf ball to a printing station, and printing a first indicia on the golf ball. Then, the golf ball is rotated and a second indicia is printed on the golf ball. Next, the golf ball, with the first and second indicia thereon, is transferred to a first camera station of a vision inspection device. Next, the golf ball is oriented to position the first indicia in the view of a first camera, and an image of the first indicia is captured by the first camera and analyzed by the computer imaging program. Next, the golf ball, with the first and second indicia thereon, is transferred to a second camera station of the vision inspection device. Then, the golf ball is oriented to position the second indicia in the view of a second camera, and an image of the second indicia captured by the second camera and analyzed by the computer imaging program. Next, the golf ball, with the first and second indicia thereon, is transferred to a curing station if the analysis of the images of the first and second indicia are within acceptable parameters.

Another aspect of the present invention is a system for printing and inspection of an indicia on a golf ball. The system includes a conveyance line, a printing station, a vision inspection station and a curing station. At the printing station, a first indicia and a second indicia is printed on each of the plurality of golf balls. The printing station is disposed on the conveyance line. The vision inspection station is disposed on the conveyance line subsequent to the printing station. The vision inspection station includes a plurality of cameras disposed in relation to the conveyance line for capturing an image of the indicia on the golf ball for analysis. The system also includes a means for determining acceptable indicia and unacceptable indicia. Finally, the curing station is disposed subsequent to the vision inspection station.

Having briefly described the present invention, the above and further objects, features and advantages thereof will be recognized by those skilled in the pertinent art from the following detailed description of the invention when taken in conjunction with the accompanying drawings.

BRIEF DESCRIPTION OF THE SEVERAL VIEWS OF THE DRAWINGS

FIG. 2 is a top plan view of FIG. 1.

FIG. 3 is an isolated front view of the printing system of FIG. 1

DETAILED DESCRIPTION OF THE INVENTION

Figure 1:
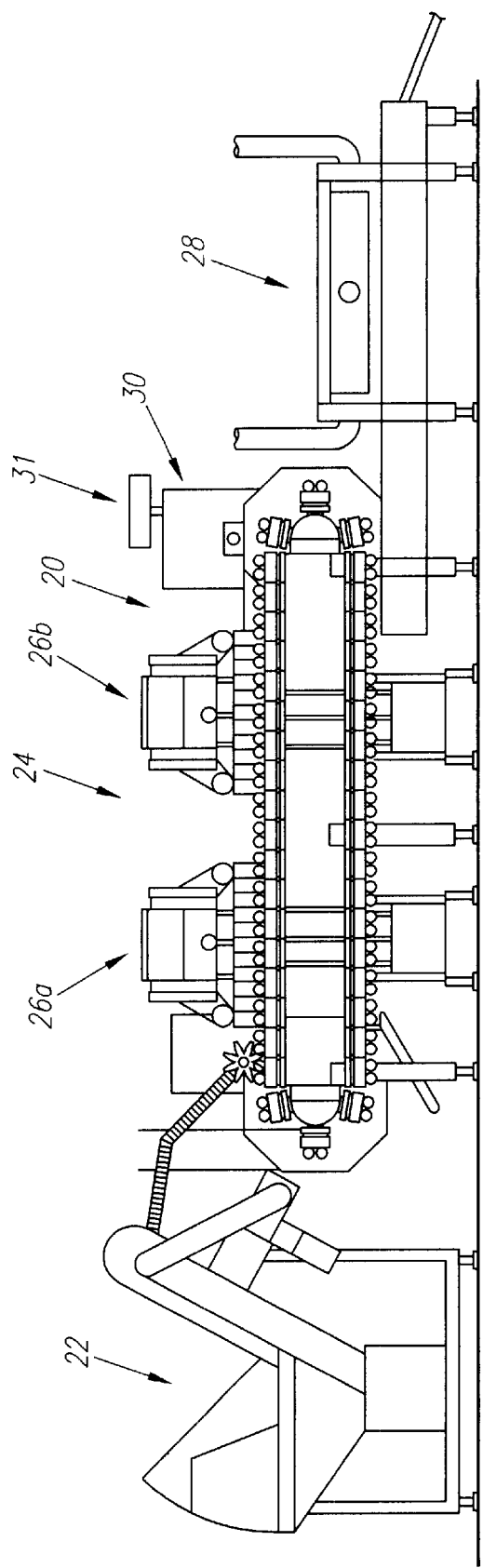
FIG. 1 is a side view of a printing system that utilizes the vision inspection system of the present invention.

As shown in FIG. 1, an indicia printing system is generally designated 20. The indicia printing system 20 is constructed to mark an identifying indicia or logo on a golf ball. More likely than not, one of the indicia or logos will indicate a company name and/or a well-known brand name. Thus, it is important that the indicia is printed perfect or near perfect since the appearance of the indicia will be associated with quality of golf ball, and logically the quality of the company that produces the golf ball.

The system generally includes a golf ball source 22, a conveyor line 24, a printing station 26, a curing station 28, and in-line vision inspection station 30 of the present invention. The in-line vision inspection station 30 is positioned between the printing station 26 and the curing station 28. The conveyor line 24 transfers golf balls 32 from the golf ball source to the printing station 26 for indicia printing, then the conveyor line 24 transfers the golf balls 32 to the vision inspection station 30. At the vision inspection station 30, the quality of the indicia is determined for each golf ball 32, and each indicia. If the indicia printed on the golf balls 32 are acceptable, then the conveyor line 24 transfers the golf balls 32 to the curing station 28. Unacceptable golf balls 32 are transferred to an indicia removal station 34 for removal of the unacceptable indicia.

Each golf ball 32 is transferred from the source 22, which is typically a hopper, to a golf ball holder 38. The source 22 accumulates the golf balls 32 subsequent to the painting of the golf balls 32 with a base coat or clear coat. Alternatively, the source 22 accumulates golf balls 32 subsequent to molding a doped cover material (doped with a whitening agent such as titanium dioxide).

The conveyor line 24 is composed of a plurality of golf ball holders 38 that are interconnected to form a chain-like mechanism on the conveyor line 24. Two adjacent golf ball holders 38 are positioned on a plate 56 which is connected to other plates 56 by connectors 58 to form a chain of plates 56. The chain of plates 56 also forms two parallel lines of golf ball holders 38. As shown in FIGS. 8–11, each golf ball holder 38 is composed of a U-shaped frame body 40. The U-shaped frame body has two upward extending arms 42a and 42b. On the interior surface of each of the arms 42a–b is an engagement member 44a–b. Each pair of engagement members 44a–b secure a golf ball 32 within the holder 38.

The engagement members 44a–b rotate the golf ball 32 about a imaginary central axis 60 through the golf ball 32.

The fixed and controlled rotation of the golf ball 32 allows for indicia printing at several different locations on the surface 48 of the golf ball 32 as the golf ball 32 is conveyed from a first ink transfer pad 36a to a second ink transfer pad 36b to a third ink transfer pad 36c. As shown in FIGS. 4–7, each time that the golf ball 32 is conveyed to an ink transfer pad 36, the golf ball 32 is rotated for printing on an unprinted portion of the surface 48 of the golf ball 32. The rotation is controlled and repeatable in order to inspect the indicia printing at the vision inspection station 30. The rotation preferably ranges from 10 degrees to 320 degrees, more preferably from 45 degrees to 270 degrees, and most preferably from 90 degrees to 180 degrees. Each golf ball 32 is held within a holder 38 throughout the indicia printing and the vision inspection of the golf ball 32.

Figure 4:
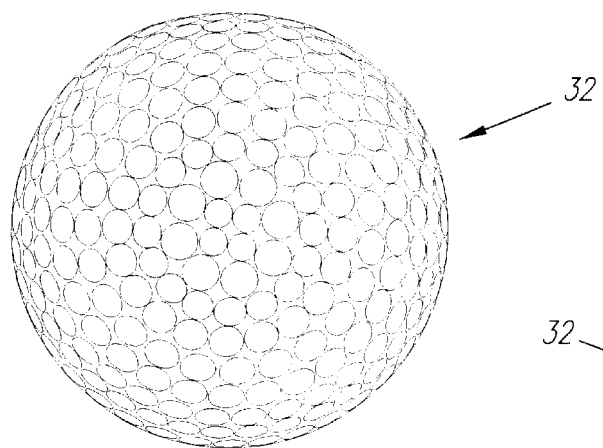
FIG. 4 is an unprinted golf ball.
Figure 5:
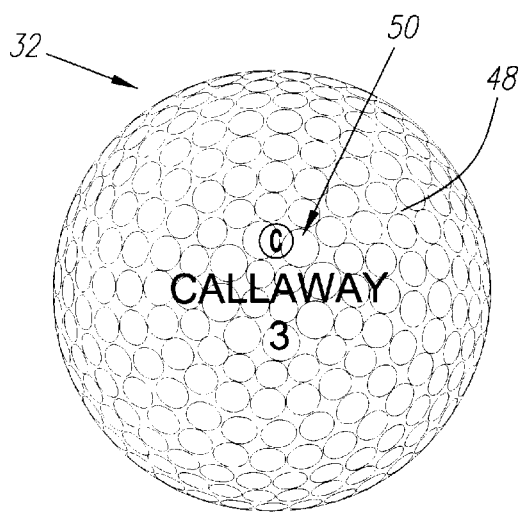
FIG. 5 is a golf ball with a first indicia printed thereon.
Figure 6:
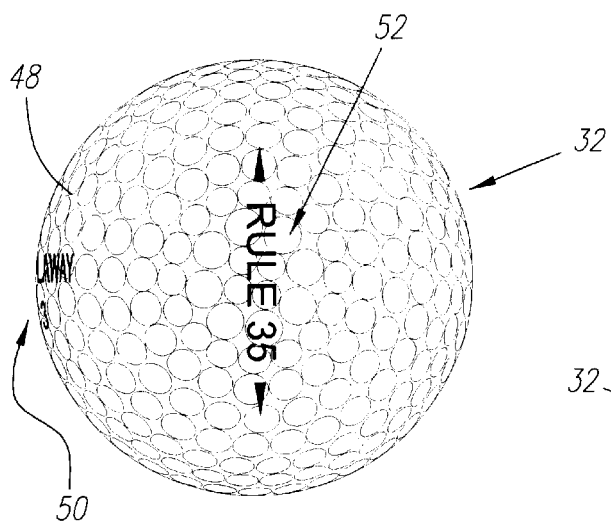
FIG. 6 is a golf ball with a first indicia and second indicia printed thereon.
Figure 7:
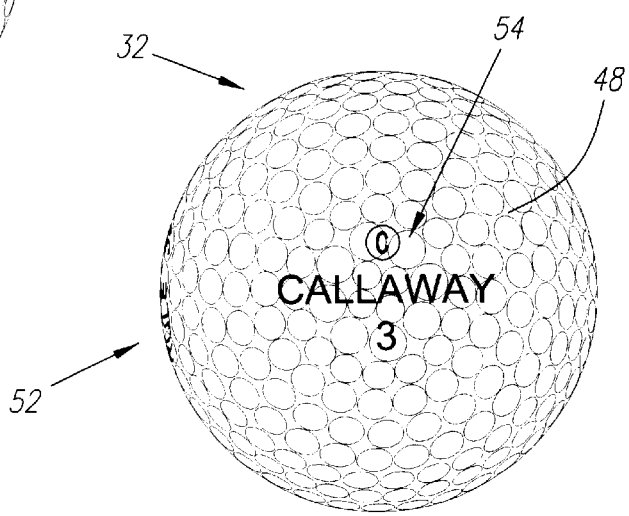
FIG. 7 is a golf ball with a first indicia, second indicia and third indicia printed thereon.
Figure 8:
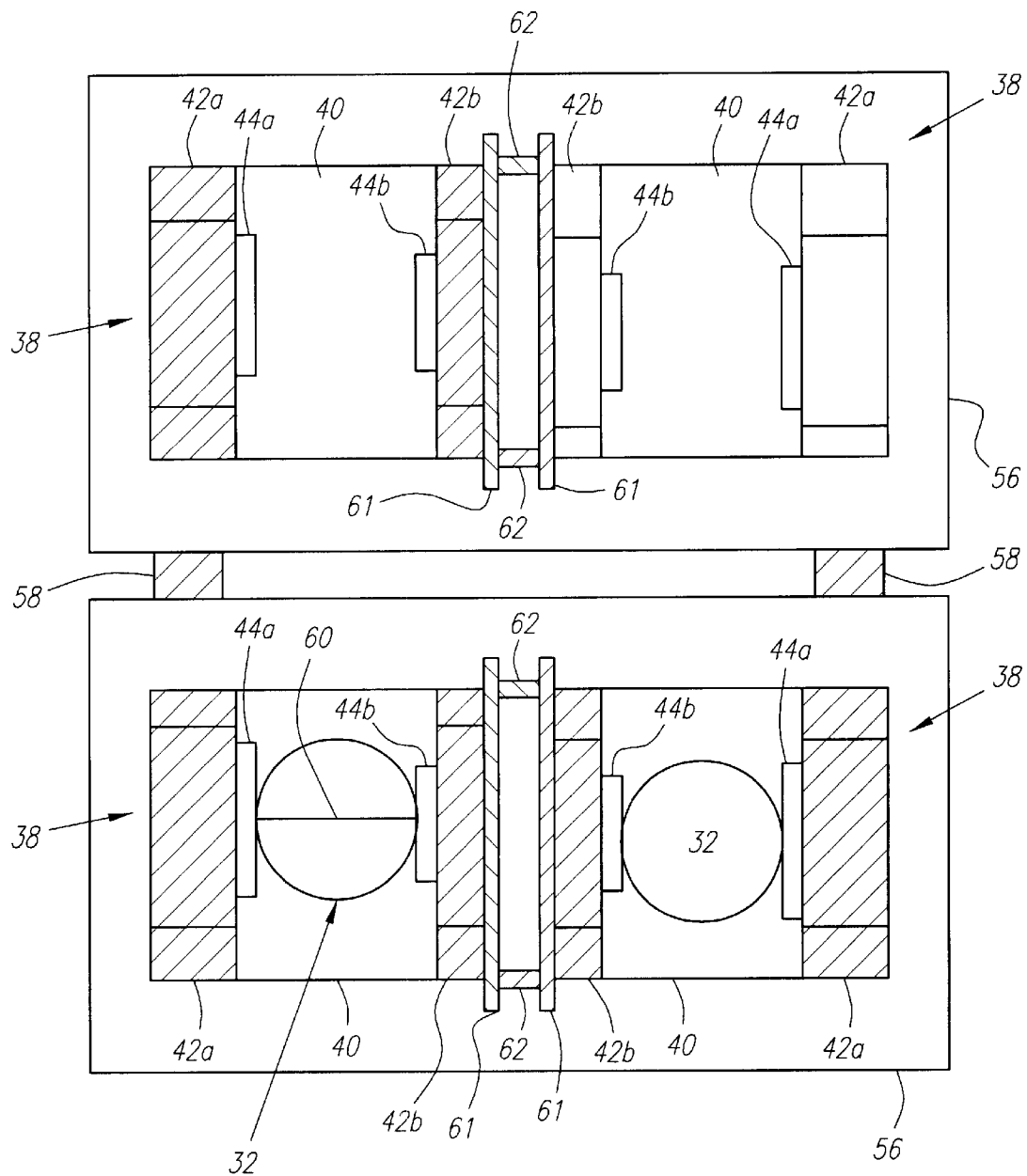
FIG. 8 is an isolated top view of a golf ball holder utilized with the present invention.
Figure 9:
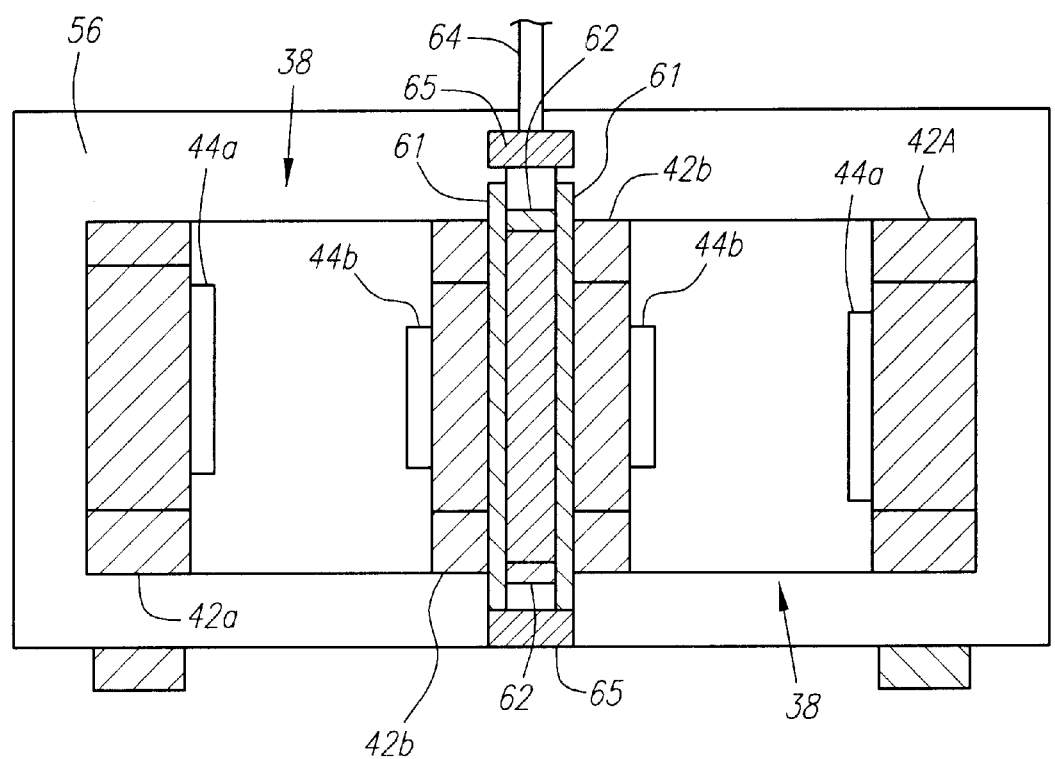
FIG. 9 is an isolated top view of a golf ball holder with a gear bar disposed above.
Figure 10:
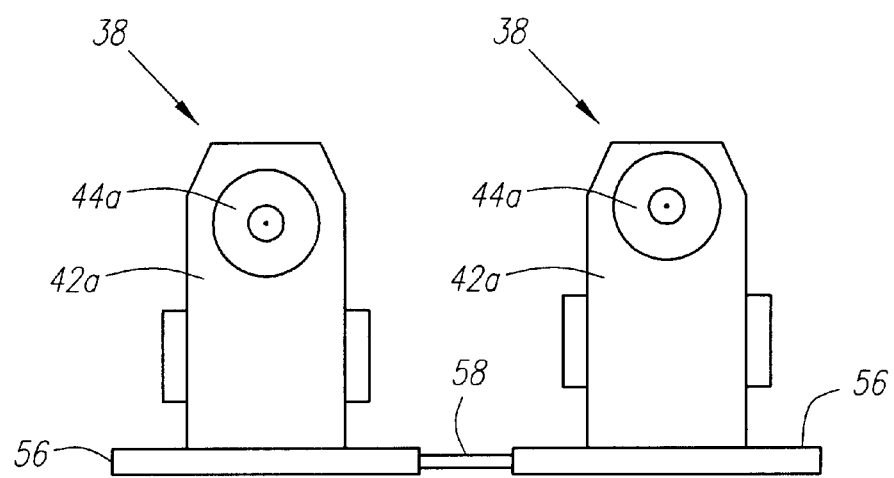
FIG. 10 is a side view of a series of golf ball holders.
Figure 11:
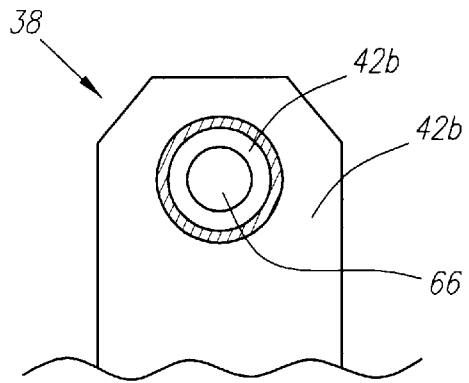
FIG. 11 is an isolated side view of the interior wall of a golf ball holder.
Figure 12:
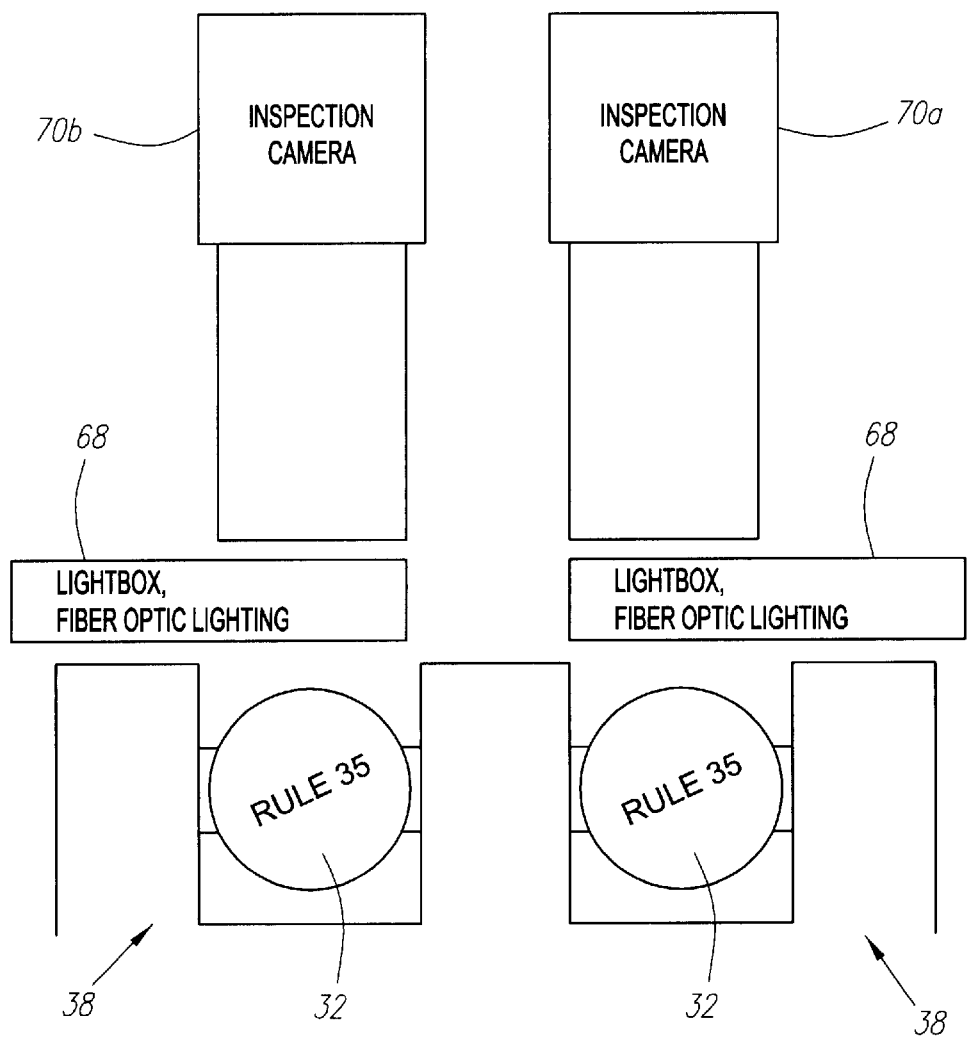
FIG. 12 is an isolated front view of the vision inspection station.

FIG. 4 illustrates an unprinted golf ball 32. The golf ball 32 may be a two-piece or multiple-piece golf ball, with a painted cover, or an unpainted cover such as an ionomer cover doped with titanium dioxide for coloring. The cover of the golf ball 32 is typically white, however, other colors may be used in practicing the present invention. FIG. 5 illustrates a first indicia 50 that has been printed of the surface 48 of the golf ball 32. At FIG. 6, the golf ball 32 is rotated ninety degrees about the central axis 60 and a second indicia 52 is printed on the golf ball 32. The first indicia 50 is still visible. At FIG. 7, the golf ball 32 is rotated another ninety degrees about the central axis 60 and a third indicia 54 is printed on the golf ball 32. The second indicia 52 is still slightly visible.

A preferred printing station 26 is a transfer pad printing station in which transfer pads 36 transfer an ink image of an indicia to the golf ball 32. Such a transfer pad printer is available from TransTech Company of Carol Stream, Ill. under the brand name SIRUIS 130. A most preferred printing station 26 is one that uses an ultraviolet ("UV") curable ink for transferring the ink image of an indicia to the golf ball 32. A preferred ink is an UV curable ink sold under the trade name UVAB and available from Trans Tech of Carol Stream, Ill. The ink includes an UV curable resin, a coloring agent, a pigment/dye and a photoinitiator. Another UV curable ink is sold under the trade name PRISMFLEX and is available from Sun Chemical. However, those skilled in the pertinent art will recognize other conventional printing means could be used without departing from the scope and spirit of the vision inspection system of the present invention. One alternative would be to use a transfer pad printing with an alternative ink such as a single component ink.

Returning to FIGS. 8 and 9, each pair of adjacent golf ball holders 38 on a single plate 56 are positioned opposite to each other. A connection wall 61 of each golf ball holder 38 is attached to an adjacent connection wall 61 of the adjacent golf ball holder 38 by a common transition wheel 62. Each transition wheel 62 lies under a cam bar 64 that has a plurality of cam pins 65 projecting downward therefrom. The cam pins 65 engage the transition wheel 62 during the conveyance of the golf ball holders 32 through the printing station 26 and through the vision inspection station 30. The transition wheel 62 is rotated ninety degrees by the cam pin 65 thereby rotating the engagement member 44b, and eventually the golf ball 32.

In the vision inspection station 30, a plurality cameras 70 are mounted above the lines of conveyance 24. In a preferred vision inspection station 30 there are four cameras 70 mounted above each line of conveyance to capture each indicia that has been printed on the golf ball 32. A fiber optic lighting device 68 provides the necessary lighting for imaging of the indicia 50 below the camera. The plurality of cameras 70 are preferably all CCD cameras.

Figure 13:
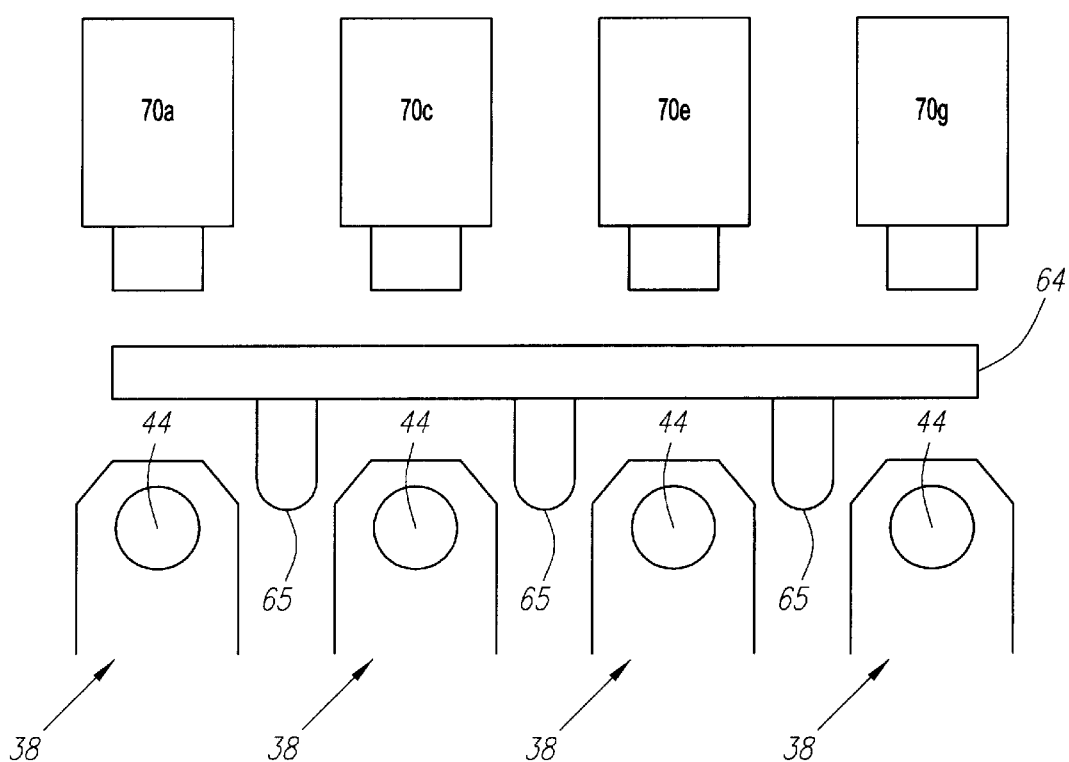
FIG. 13 is an isolated side view of the vision inspection station.
Figure 14:
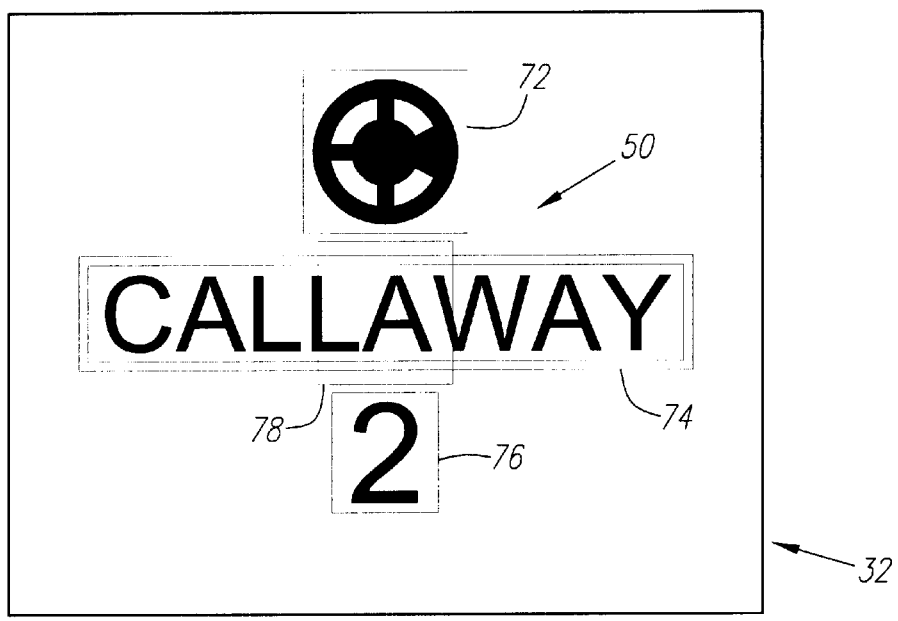
FIG. 14 is a view of the image of an indicia captured by the vision inspection station.
Figure 15:
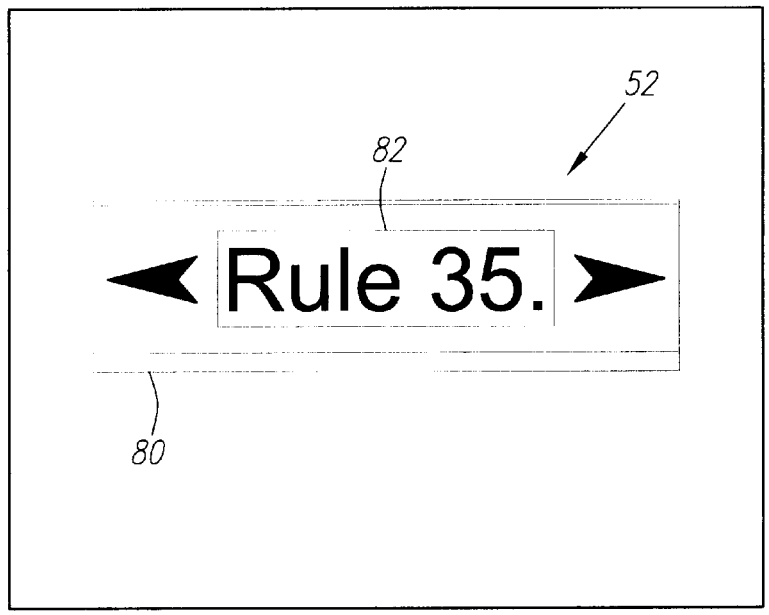
FIG. 15 is a view of the image of a second indicia captured by the vision inspection station.

As shown in FIG. 13, four cameras 70a, 70c, 70e, 70g are mounted above the line of conveyance 24. Each golf ball holder 38 pauses for a predetermined period of time underneath a first camera 70a in order for an image of the indicia 50 to be captured as shown in FIG. 14, and then analyzed by a computer software program. Such a computer software program is available from Systech Solutions, Inc. of Cranbury, N.J. The rate of conveyance may preferably vary from 50–100 golf balls per minute. As the golf ball holder moves to the next camera 70c, it is rotated ninety degrees by the cam pin 65 transition wheel 62 mechanism, or some similar mechanism. An image as shown in FIG. 15 of the second indicia 52 is captured and analyzed by a computer software program. This process continues for the other indicia at the other camera substations.

The computer imaging program looks at different image boxes 72–82 to determine if the indicia 50 meets a predetermined standard for such an indicia. The indicia 50 may preferably range in height from 0.05 inch to 0.20 inch, and may preferably vary in length from 0.10 inch to 1.04 inches. The color of each indicia 50, 52 and 54 may be any visible or detectable color, and the indicia 50 may be composed of different colors. The computer imaging program also analyzes the pixel content, the positioning of the text and characters of the indicia 50, the intensity, and other like properties. More specifically, the vision inspection system detects flaws as minimal as 0.001 inch square on an image box 72–82 of 10 inch square. The flaws include detection of an absence of ink in an image box 72–82 where ink should be present, or the detection of the presence of ink in an image box 72–82 where ink should not be present. The vision inspection system also detects flaws in the structure of the cover of the golf ball 32, and flaws in the paint on the golf ball 32. The vision inspection system is also capable of having each camera 70 track the location of he indicia 50 on the golf ball up to a variance of five degrees.

If the golf ball 32 is acceptable, the golf ball 32 is transferred from the primary conveyor line 24 to a curing station conveyor line 46. If the golf ball 32 is unacceptable, the golf ball 32 is transferred to the indicia removal station 34, not shown. The curing station conveyor line 46 transfers the golf ball 32 to a curing station 28. Preferably the ink for the first, second and third indicia 50, 52 and 54 is an ultraviolet curable ink, and the curing station 28 is a ultraviolet energy curing station having an ultraviolet light lamp disposed above the curing station conveyor line 46 to cure each of the first, second and third indicia 50, 52 and 54. However, those skilled in the pertinent art will recognize that other inks and corresponding curing stations may be used without departing from the scope and spirit of the present invention.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes, modifications and substitutions of equivalents may be made therein without departing from the spirit and scope of this invention which is intended to be unlimited by the foregoing except as may appear in the following appended claims. Therefore, the embodiments of the invention in which an exclusive property or privilege is claimed are defined in the following appended claims.

We claim as our invention:

1. A method for inspecting golf ball indicia, the method comprising:

printing a first and second indicia on a golf ball at a printing station;

transferring the golf ball to a vision inspection station, the golf ball having indicia thereon;

maneuvering the golf ball to position the indicia within viewing of a first camera within the vision inspection system;

scanning the indicia and transferring an image of the indicia to a computer for inspection of the indicia; and analyzing the image to determine if the indicia is within acceptable parameters;

transferring the golf ball to a second camera within the vision inspection station;

maneuvering the golf ball to position the second indicia within viewing of the second camera;

scanning the second indicia and transferring an image of the second indicia to a computer for inspection of the indicia; and analyzing the image to determine if the second indicia is within acceptable parameters.

2. The method according to claim 1 wherein the images of the first and second indicia are analyzed for pixel content of the each indicia as compared to a reference image of each indicia.

3. The method according to claim 1 wherein the images of the first and second indicia are analyzed for placement within a predetermined area projected on the image.

4. The method according to claim 3 further comprising transferring the golf ball with the first and second indicia thereon to a rejection station if the analysis of the images of the first and second indicia are not within acceptable parameters.

5. The method according to claim 1 wherein the first and second indicia are composed of a UV curable ink.

6. The method according to claim 1 further comprising:

printing a third indicia on the golf ball prior to transferring the golf ball to the vision inspection station;

orienting the golf ball to position the third indicia in the view of a third camera at a third camera station subsequent to analyzing the second indicia; and analyzing an image of the third indicia captured by the third camera.

7. The method according to claim 1 further comprising curing the first and second indicia if the indicia are within acceptable parameters.

8. A method for in-line inspection of golf ball indicia, the method comprising:

transferring a golf ball to a printing station;

printing a first indicia on the golf ball;

rotating the golf ball and printing a second indicia on the golf ball;

transferring the golf ball with the first and second indicia thereon to a first camera station of a vision inspection device;

orienting the golf ball to position the first indicia in the view of a first camera;

analyzing an image of the first indicia captured by the first camera;

transferring the golf ball with the first and second indicia thereon to a second camera station of the vision inspection device;

orienting the golf ball to position the second indicia in the view of a second camera;

analyzing an image of the second indicia captured by the second camera;

transferring the golf ball with the first and second indicia thereon to a curing station if the analysis of the images of the first and second indicia are within acceptable parameters.

9. The method according to claim 8 further comprising transferring the golf ball with the first and second indicia thereon to a rejection station if the analysis of the images of the first and second indicia are not within acceptable parameters.

10. The method according to claim 8 wherein the first and second indicia are composed of a UV curable ink.

11. The method according to claim 8 further comprising:

printing a third indicia on the golf ball prior to transferring the golf ball to the first camera station;

orienting the golf ball to position the third indicia in the view of a third camera at a third camera station subsequent to analyzing the second indicia; and analyzing an image of the third indicia captured by the third camera.

12. The method according to claim 8 wherein the images of the first and second indicia are analyzed for pixel content of the each indicia as compared to a reference image of each indicia.

13. The method according to claim 8 wherein the images of the first and second indicia are analyzed for placement within a predetermined area projected on the image.

14. A system for printing and inspection of an indicia on a golf ball, the system comprising:

a conveyance line for conveying a plurality of golf balls;

a printing station for printing a first indicia and a second indicia on each of the plurality of golf balls, the printing station disposed on the conveyance line;

a vision inspection station disposed on the conveyance line subsequent to the printing station, the vision inspection station comprising a plurality of cameras disposed in relation to the conveyance line for capturing an image of the indicia on the golf ball for analysis;

means for determining acceptable indicia and unacceptable indicia; and means for curing the first and second indicia on the golf ball, the curing means disposed subsequent to the vision inspection station.

15. The system according to claim 14 wherein the first and second indicia are composed of UV curable ink, and the curing means is a UV light disposed within a protective housing.

* * * * *